US00PP13085P2

(12) United States Plant Patent
Gainous

(10) Patent No.: US PP13,085 P2
(45) Date of Patent: Oct. 15, 2002

(54) DOGWOOD TREE NAMED 'GOLD BRAID'

(75) Inventor: Jimmy Leland Gainous, Cairo, GA (US)

(73) Assignee: Gainous' Shade Trees, Inc., Cairo, GA (US)

( * ) Notice: Subject to any disclaimer, the term of this patent is extended or adjusted under 35 U.S.C. 154(b) by 1 day.

(21) Appl. No.: 09/774,368

(22) Filed: Feb. 1, 2001

(65) Prior Publication Data

US 2002/0104136 P1 Aug. 1, 2002

(51) Int. Cl.[7] ..... A01H 5/00

(52) U.S. Cl. ..... Plt./220

(58) Field of Search ..... Plt./220

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Dogwood tree named 'Gold Braid', characterized by its upright pyramidal plant shape; unique yellow and green variegated foliage; long-lasting leaf variegation pattern; foliage that resists sunburning; and resistance to late-season spot Anthracnose.

3 Drawing Sheets

BOTANICAL CLASSIFICATION

*Cornus florida* cultivar Gold Braid.

BACKGROUND OF THE INVENTION

The present Invention relates to a new and distinct cultivar of Dogwood tree, botanically known as *Cornus florida*, and hereinafter referred to by the name 'Gold Braid'.

The new Dogwood was discovered by the Inventor in a controlled environment in Cairo, Ga., during 1994 as a chance seedling of two unidentified selections of *Cornus florida*.

Asexual reproduction of the new Dogwood by cuttings in a controlled environment in Tifton, Ga. since 1994, has shown that the unique features of this new Dogwood are stable and reproduced true to type in successive generations.

SUMMARY OF THE INVENTION

The cultivar 'Gold Braid' has not been observed under all possible environmental conditions. The phenotype may vary somewhat with variations in environment such as temperature, daylength, light intensity, and water and nutritional status without, however, any variance in genotype.

The following traits have been repeatedly observed and are determined to be the unique characteristics of 'Gold Braid'. These characteristics in combination distinguish 'Gold Braid' as a new and distinct Dogwood:

1. Upright pyramidal plant shape.

2. Unique yellow and green variegated foliage; leaf variegation pattern is relatively long-lasting and does not fade.

3. Foliage resists sunburning.

4. Resistant to late-season spot Anthracnose.

In side-by-side comparisons conducted in Tifton, Ga., trees of the new Dogwood differ from trees of the unidentified selections and from other known variegated Dogwood cultivars primarily in its longer-lasting leaf variegation pattern.

BRIEF DESCRIPTION OF THE PHOTOGRAPHS

The accompanying colored photographs illustrate the overall appearance of the new Dogwood, showing the colors as true as it is reasonably possible to obtain in colored reproductions of this type. Colors in the photographs may differ slightly from the color values cited in the detailed botanical description which accurately describe the colors of the new Dogwood.

The photograph on the first sheet comprises a side perspective view of a typical tree of 'Gold Braid' during the summer.

The photograph on the second sheet is a close-up view of typical leaves of 'Gold Braid' during the summer.

The photograph on the third sheet comprises a close-up view of typical flowers of 'Gold Braid'.

DETAILED BOTANICAL DESCRIPTION

In the following description, color references are made to The Royal Horticultural Society Colour Chart except where general terms of ordinary dictionary significance are used. The following observations and measurements describe trees grown in Tifton, Ga., under commercial practice in a outdoor field nursery. During the production of these trees, the mean of the warmest month was 27.2° C. and the mean of coldest month was 8.5° C. Trees measured were about four years from planting.

Botanical classification: *Cornus florida* cultivar Gold Braid.
Parentage: Seedling of two unidentified selections of *Cornus florida*, not patented.
Propagation:
- *Type.*—Softwood cuttings.
- *Root description.*—Fibrous, freely branching.

Plant description:
- *Plant form.*—Upright and pyramidal tree; fastigiate, spreading.
- *Growth rate.*—Moderate. Height: About 84 cm per year. Trunk caliper: About 1.5 cm per year.
- *Plant height.*—About 3.45 meters.

*Plant width.*—About 1.8 meters.

*Stems.*—Strength: Strong, no breakage noted. Internode length: About 3.5 to 5.5 cm on strong new growth. Texture: Short, appressed pubescence. Color: Young stems: 144C. Woody: Grayish, close to 197A.

*Leaves.*—Leaves have not been observed to sunburn under full sun conditions in Tifton, Ga. Arrangement: Simple, opposite. Length: About 7 to 11 cm. Width: About 3.5 to 5.5 cm. Shape: Elliptic. Apex: Acuminate. Base: Obtuse, may not be equilateral. Margin: Entire; undulate. Texture: Pubescence on both surfaces; somewhat rugose. Petiole length: About 1 to 2 cm. Petiole diameter: About 2 mm. Color: Variegation pattern is relatively long-lasting and does not fade. Young leaves, upper surface: Center, irregular, 146B; surrounded by 10A. Young leaves, lower surface: Center, irregular, 147C; surrounded by 8B. Mature leaves, upper surface: Center, irregular, 137A; surrounded by 13A. Mature leaves, lower surface: Center, irregular, 191B; surrounded by 8B. Autumn coloration: Variegated portions, close to 185C. Petiole: 145B.

Flower description:

*Flowering habit.*—Not freely flowering. Single flowers arranged in compact dense heads subtended by four showy bracts. Mildly sweet fragrance. Flowers not persistent. Flowers face upright or outwardly.

*Natural flowering season.*—Plants flower in Tifton, Ga. in early to mid-March. Flowers last about 3 to 4 weeks on the tree.

*Flower bud.*—Length: About 1 cm. Diameter: About 1 cm.

*Flower head size.*—Diameter: About 1.5 cm. Height: About 8 mm.

*Flower diameter* (*including bracts*).—About 5.5 to 8 cm.

*Petals.*—Quantity: Four per flower. Length: About 2 to 3 mm. Width: About 1 mm. Apex: Recurved. Margin: Entire. Color: When opening, both surfaces: 144C. Fully opened, both surfaces: 151D.

*Bracts.*—Quantity: Four per flower head. Length: About 3.8 to 5 cm. Width: About 2.5 to 3.8 cm. Shape: Obovate; petal-like. Apex: Notched. Base: Attentuate. Margin: Entire. Texture: Longitudinally ridged. Color: Towards apex, 1D; Upper surface: towards base, 145C; notch at apex, N187A. Lower surface: Close to 150D.

*Peduncles.*—Strength: Strong. Length: About 2.5 to 3.5 cm. Texture: Appressed pubescence. Color: Green, 143C.

*Reproductive organs.*—Stamens: Quantity: Four per flower. Anther size: About 1 to 1.5 mm. Anther color: Yellow, 11B. Pollen color: Yellow, 11B. Pistils: Quantity: One per flower. Length: About 2 mm. Stigma color: Yellow green, 149A. Style length: About 2 mm. Style color: Yellow green, 149A. Ovary color: Yellow, 4C.

*Fruit.*—Shape/type: Oblong drupe. Length: About 1.5 cm. Diameter: About 1 cm. Texture: Smooth. Color: 46B to 46C; glossy.

*Seed.*—Length: About 1 to 1.5 cm. Diameter: About 8 mm.

Disease resistance: Trees of the new Dogwood have been shown to be resistant to late-season spot Anthracnose.

It is claimed:

1. A new and distinct cultivar of Dogwood tree named 'Gold Braid', as illustrated and described.

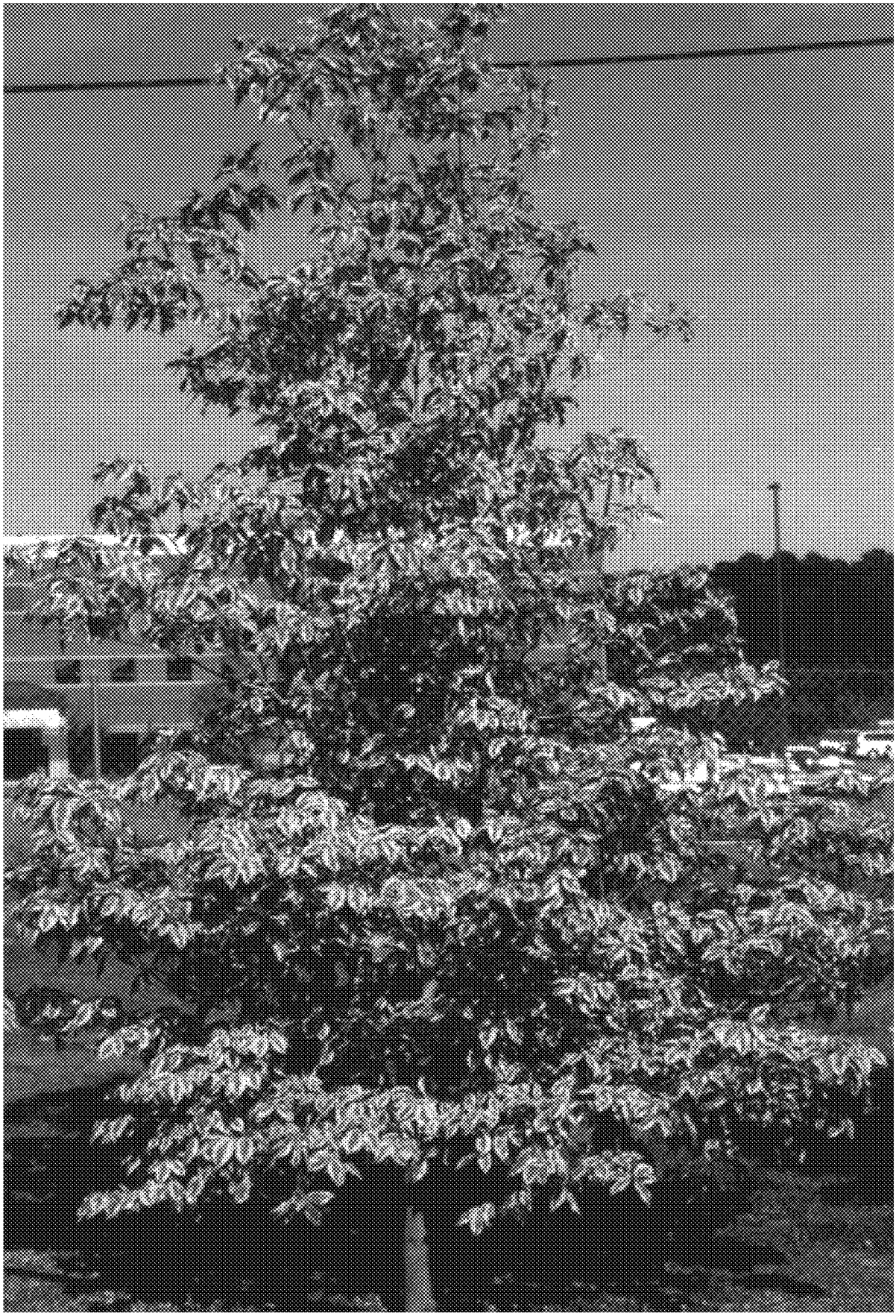

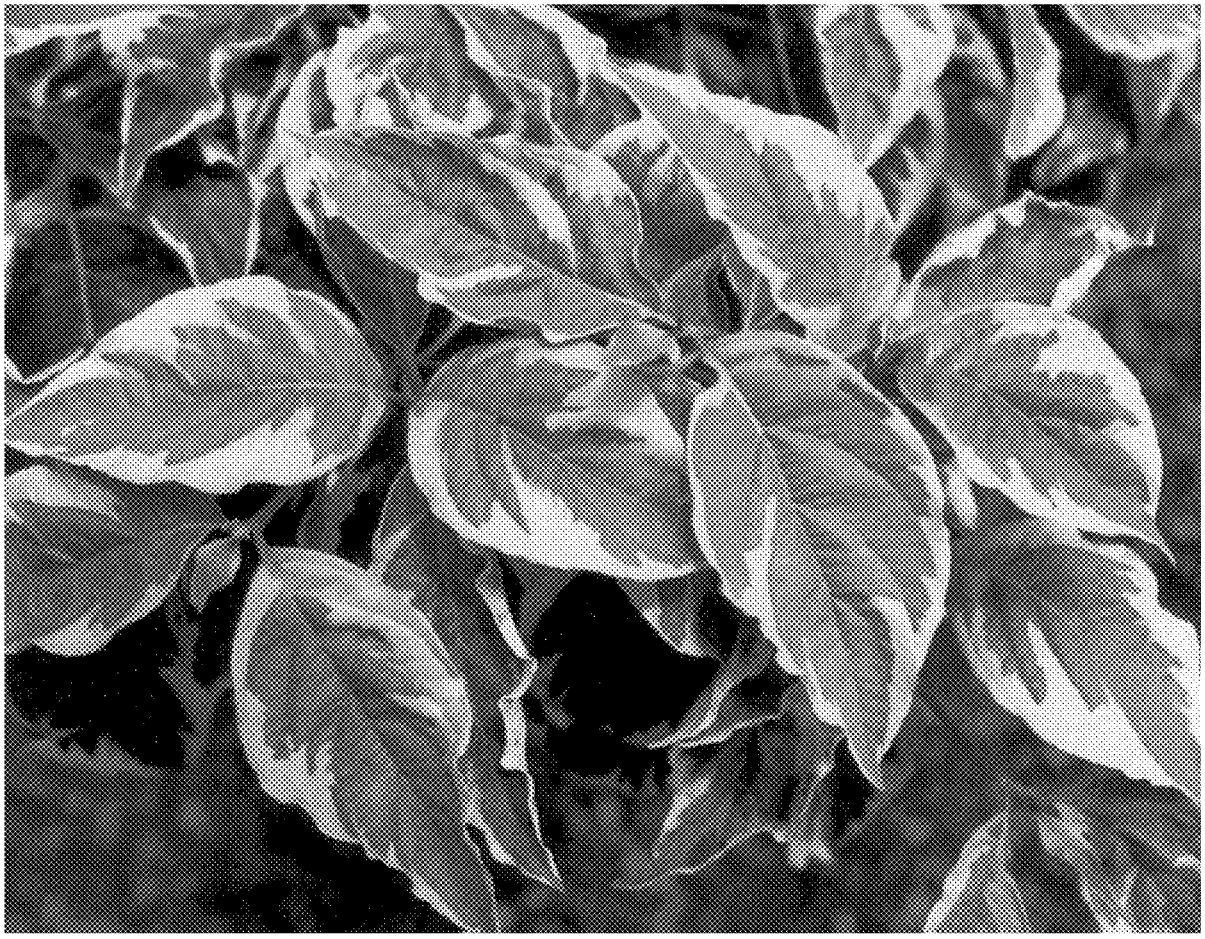

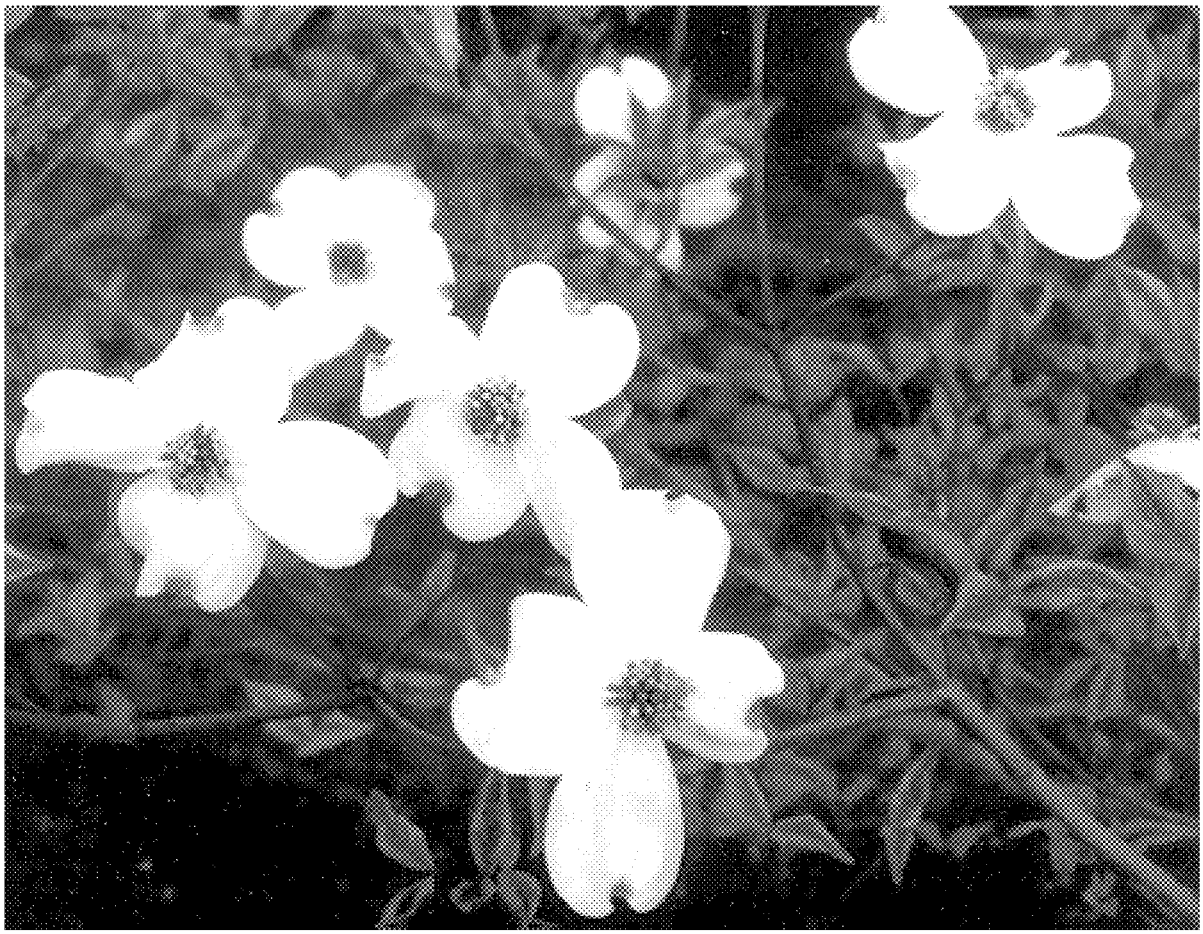

* * * * *